US012083261B2

(12) United States Patent
Justice et al.

(10) Patent No.: US 12,083,261 B2
(45) Date of Patent: Sep. 10, 2024

(54) AUTOMATED FLUID OUTPUT MONITORING

(71) Applicant: C. R. Bard, Inc., Franklin Lakes, NJ (US)

(72) Inventors: Chris Justice, Leawood, KS (US); Griffin Adams, Overland Park, KS (US); Katy Kanne, Kansas City, MO (US); Ryan Zumbach, Kansas City, MO (US); Cuong Nguyen, Kansas City, MO (US); Rob Lembke, Overland Park, KS (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/306,821

(22) Filed: May 3, 2021

(65) Prior Publication Data
US 2021/0379269 A1    Dec. 9, 2021

Related U.S. Application Data

(60) Provisional application No. 63/035,567, filed on Jun. 5, 2020.

(51) Int. Cl.
| A61M 1/00 | (2006.01) |
| A61M 25/00 | (2006.01) |
| A61M 25/10 | (2013.01) |

(52) U.S. Cl.
CPC .............. *A61M 1/69* (2021.05); *A61M 25/00* (2013.01); *A61M 25/10* (2013.01);
(Continued)

(58) Field of Classification Search
CPC ........ A61M 1/69; A61M 25/00; A61M 25/10; A61M 2205/3327; A61M 2205/3334;
(Continued)

(56) References Cited

U.S. PATENT DOCUMENTS

| 3,661,143 A | 5/1972 | Henkin |
| 3,781,920 A | 1/1974 | Browne et al. |
(Continued)

FOREIGN PATENT DOCUMENTS

| CA | 2882654 A1 | 10/2007 |
| CN | 2445749 | 9/2001 |
(Continued)

OTHER PUBLICATIONS

Bard Medical, Criticore Disposables—Non I.C., 3 pages, www.bardmedical.com/products/patienl-moniloring-, ystems/criticore®-system/criticore®disposables-non-ic/ Jan. 30, 2015.
(Continued)

*Primary Examiner* — Rebecca E Eisenberg
*Assistant Examiner* — Kate Elizabeth Strachan
(74) *Attorney, Agent, or Firm* — Rutan & Tucker LLP

(57) ABSTRACT

Embodiments disclosed herein are directed to apparatus and methods for a fluid collection system and automated fluid flow monitoring. The system can include a collection container, and a detection device coupled to an outside surface thereof and configured to detect a volume of fluid disposed therein. The detection device can be coupled to the collection container without having to compromise the integrity of the closed fluid collection system or re-catheterizing the patient. The detection device can be configured to detect an inversion event, tilt event, and the like to determine a flow rate of fluid into the container. The detection device can be communicatively coupled with external computing devices to alert a clinician when the container is nearing capacity and when it has been emptied.

19 Claims, 7 Drawing Sheets

(52) U.S. Cl.
CPC ............... *A61M 2205/3327* (2013.01); *A61M 2205/3334* (2013.01); *A61M 2205/3375* (2013.01); *A61M 2205/3389* (2013.01); *A61M 2205/3584* (2013.01)

(58) Field of Classification Search
CPC .. A61M 2205/3375; A61M 2205/3389; A61M 2205/3584; A61F 5/44; A61F 5/4404
See application file for complete search history.

(56) References Cited

U.S. PATENT DOCUMENTS

| | | |
|---|---|---|
| 3,851,650 A | 12/1974 | Darling |
| 3,919,455 A | 11/1975 | Sigdell et al. |
| 4,276,889 A | 7/1981 | Kuntz et al. |
| 4,286,590 A | 9/1981 | Murase |
| 4,291,692 A | 9/1981 | Bowman et al. |
| 4,296,749 A | 10/1981 | Pontifex |
| 4,305,405 A | 12/1981 | Meisch |
| 4,312,352 A | 1/1982 | Meisch et al. |
| 4,343,316 A | 8/1982 | Jespersen |
| 4,443,219 A | 4/1984 | Meisch et al. |
| 4,448,207 A | 5/1984 | Parrish |
| 4,509,366 A | 4/1985 | Matsushita et al. |
| 4,532,936 A | 8/1985 | LeVeen et al. |
| 4,658,834 A | 4/1987 | Blankenship et al. |
| 4,723,950 A | 2/1988 | Lee |
| 4,834,706 A | 5/1989 | Beck et al. |
| 4,850,375 A | 7/1989 | Rosenberg |
| 4,889,532 A | 12/1989 | Metz et al. |
| 5,002,541 A | 3/1991 | Conkling et al. |
| 5,409,014 A | 4/1995 | Napoli et al. |
| 5,586,085 A | 12/1996 | Lichte |
| 5,725,515 A | 3/1998 | Propp |
| 5,733,319 A | 3/1998 | Neilson et al. |
| 5,738,656 A | 4/1998 | Wagner |
| 5,747,824 A | 5/1998 | Jung et al. |
| 5,769,087 A | 6/1998 | Westphal et al. |
| 5,807,278 A | 9/1998 | McRae |
| 5,823,972 A | 10/1998 | McRae |
| 5,891,051 A * | 4/1999 | Han ..................... A61B 5/208 600/580 |
| 5,911,786 A | 6/1999 | Nielsen et al. |
| 6,129,684 A | 10/2000 | Sippel et al. |
| 6,132,407 A | 10/2000 | Genese et al. |
| 6,250,152 B1 | 6/2001 | Klein et al. |
| 6,256,532 B1 | 7/2001 | Cha |
| 6,261,254 B1 | 7/2001 | Baron et al. |
| 6,434,418 B1 | 8/2002 | Neal et al. |
| 6,579,247 B1 | 6/2003 | Abramovitch et al. |
| 6,592,612 B1 | 7/2003 | Samson et al. |
| 6,709,420 B1 | 3/2004 | Lincoln et al. |
| 6,716,200 B2 | 4/2004 | Bracken et al. |
| 7,011,634 B2 | 3/2006 | Paasch et al. |
| 7,161,484 B2 | 1/2007 | Tsoukalis |
| 7,211,037 B2 | 5/2007 | Briggs et al. |
| 7,437,945 B1 | 10/2008 | Feller |
| 7,442,754 B2 | 10/2008 | Tepper et al. |
| 7,739,907 B2 | 6/2010 | Boiarski |
| 7,871,385 B2 | 1/2011 | Levinson |
| 7,931,630 B2 | 4/2011 | Nishtala et al. |
| 7,976,533 B2 | 7/2011 | Larsson |
| 7,998,126 B1 | 8/2011 | Fernandez |
| 8,295,933 B2 | 10/2012 | Gerber et al. |
| 8,328,733 B2 | 12/2012 | Forte et al. |
| 8,328,734 B2 | 12/2012 | Salvadori et al. |
| 8,337,476 B2 | 12/2012 | Greenwald et al. |
| 8,374,688 B2 | 2/2013 | Libbus et al. |
| 8,403,884 B2 | 3/2013 | Nishtala |
| 8,471,231 B2 | 6/2013 | Paz |
| 8,663,128 B2 | 3/2014 | Paz et al. |
| 8,773,259 B2 | 7/2014 | Judy et al. |
| 8,790,277 B2 | 7/2014 | Elliott et al. |
| 8,790,320 B2 | 7/2014 | Christensen |
| 8,790,577 B2 | 7/2014 | Mizumoto et al. |
| 8,813,551 B2 | 8/2014 | Boiarski |
| 8,827,924 B2 | 9/2014 | Paz et al. |
| 8,832,558 B2 | 9/2014 | Cardarelli et al. |
| 8,900,196 B2 | 12/2014 | Andino |
| 9,045,887 B2 | 6/2015 | O'Malley |
| 9,050,046 B2 | 6/2015 | Elliott et al. |
| 9,074,920 B2 | 7/2015 | Mendels et al. |
| 9,216,242 B2 | 12/2015 | Nishtala et al. |
| 9,480,821 B2 | 11/2016 | Ciccone et al. |
| 9,592,034 B2 | 3/2017 | Hall et al. |
| 9,642,987 B2 | 5/2017 | Bierman et al. |
| 9,731,097 B2 | 8/2017 | Andino et al. |
| 9,895,095 B2 | 2/2018 | Chen |
| 9,962,516 B2 | 5/2018 | Lampotang et al. |
| 10,182,747 B2 | 1/2019 | Charlez et al. |
| 10,245,008 B2 | 4/2019 | Paige |
| 10,362,981 B2 | 7/2019 | Paz et al. |
| 10,383,606 B1 | 8/2019 | McCord et al. |
| 10,448,875 B2 | 10/2019 | Holt et al. |
| 10,881,778 B2 | 1/2021 | Scarpaci et al. |
| 11,703,365 B2 | 7/2023 | Tourchak et al. |
| 2001/0056226 A1 | 12/2001 | Zodnik et al. |
| 2002/0016719 A1 | 2/2002 | Nemeth et al. |
| 2002/0161314 A1 | 10/2002 | Sarajarvi |
| 2002/0193760 A1 | 12/2002 | Thompson |
| 2003/0000303 A1 | 1/2003 | Livingston et al. |
| 2003/0163183 A1 | 8/2003 | Carson |
| 2003/0163287 A1 | 8/2003 | Vock et al. |
| 2004/0267086 A1* | 12/2004 | Anstadt ............... A61M 60/289 600/17 |
| 2005/0020958 A1 | 1/2005 | Paolini et al. |
| 2005/0065583 A1 | 3/2005 | Voorhees et al. |
| 2005/0172712 A1 | 8/2005 | Nyce |
| 2005/0247121 A1 | 11/2005 | Pelster |
| 2006/0100743 A1 | 5/2006 | Townsend et al. |
| 2007/0010797 A1 | 1/2007 | Nishtala et al. |
| 2007/0145137 A1 | 6/2007 | Mrowiec |
| 2007/0252714 A1 | 11/2007 | Rondoni et al. |
| 2008/0312556 A1 | 12/2008 | Dijkman |
| 2009/0056020 A1 | 3/2009 | Caminade et al. |
| 2009/0099629 A1 | 4/2009 | Carson et al. |
| 2009/0157430 A1 | 6/2009 | Rule et al. |
| 2009/0287170 A1 | 11/2009 | Otto |
| 2009/0315684 A1 | 12/2009 | Sacco et al. |
| 2010/0094204 A1 | 4/2010 | Nishtala |
| 2010/0130949 A1 | 5/2010 | Garcia |
| 2010/0137743 A1 | 6/2010 | Nishtala et al. |
| 2011/0113540 A1 | 5/2011 | Plate et al. |
| 2011/0120219 A1 | 5/2011 | Barlesi et al. |
| 2011/0178425 A1 | 7/2011 | Nishtala et al. |
| 2011/0224636 A1 | 9/2011 | Keisic |
| 2011/0230824 A1 | 9/2011 | Salinas et al. |
| 2011/0238042 A1 | 9/2011 | Davis et al. |
| 2011/0251572 A1 | 10/2011 | Nishtala et al. |
| 2011/0263952 A1 | 10/2011 | Bergman et al. |
| 2012/0029408 A1 | 2/2012 | Beaudin |
| 2012/0059286 A1 | 3/2012 | Hastings et al. |
| 2012/0078137 A1 | 3/2012 | Mendels et al. |
| 2012/0078235 A1 | 3/2012 | Martin et al. |
| 2012/0095304 A1 | 4/2012 | Biondi |
| 2012/0109008 A1 | 5/2012 | Charlez et al. |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0234434 A1 | 9/2012 | Woodruff et al. |
| 2012/0302917 A1 | 11/2012 | Fitzgerald et al. |
| 2012/0323144 A1 | 12/2012 | Coston et al. |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |

(56) References Cited

U.S. PATENT DOCUMENTS

| | | | |
|---|---|---|---|
| 2014/0207085 A1 | 7/2014 | Brandt et al. | |
| 2014/0243635 A1* | 8/2014 | Arefieg | A61B 5/150854 600/365 |
| 2014/0335490 A1 | 11/2014 | Baarman et al. | |
| 2015/0120321 A1 | 4/2015 | David et al. | |
| 2015/0343173 A1 | 12/2015 | Tobescu et al. | |
| 2015/0359522 A1 | 12/2015 | Recht et al. | |
| 2015/0362351 A1 | 12/2015 | Joshi et al. | |
| 2016/0051176 A1 | 2/2016 | Ramos et al. | |
| 2016/0183819 A1 | 6/2016 | Burnett et al. | |
| 2017/0043089 A1 | 2/2017 | Handler | |
| 2017/0001000 A1 | 4/2017 | Kostov | |
| 2017/0100068 A1 | 4/2017 | Kostov | |
| 2017/0113000 A1 | 4/2017 | Tobescu et al. | |
| 2017/0136209 A1 | 5/2017 | Burnett et al. | |
| 2017/0196478 A1 | 7/2017 | Hunter | |
| 2017/0202698 A1 | 7/2017 | Zani et al. | |
| 2017/0249445 A1 | 8/2017 | Devries et al. | |
| 2017/0290540 A1 | 10/2017 | Franco | |
| 2017/0291012 A1 | 10/2017 | Iglesias | |
| 2017/0307423 A1 | 10/2017 | Pahwa et al. | |
| 2018/0015251 A1 | 1/2018 | Lampotang et al. | |
| 2018/0280236 A1 | 10/2018 | Ludin et al. | |
| 2018/0344234 A1 | 12/2018 | Mckinney et al. | |
| 2019/0046102 A1 | 2/2019 | Kushnir et al. | |
| 2019/0069829 A1 | 3/2019 | Bulut | |
| 2019/0069830 A1 | 3/2019 | Holt et al. | |
| 2019/0126006 A1 | 5/2019 | Rehm et al. | |
| 2019/0201596 A1 | 7/2019 | Luxon et al. | |
| 2019/0223844 A1 | 7/2019 | Aboagye et al. | |
| 2019/0247236 A1* | 8/2019 | Sides | A61F 13/0216 |
| 2019/0003215 A1 | 10/2019 | Burnett et al. | |
| 2019/0321588 A1 | 10/2019 | Burnett et al. | |
| 2019/0328945 A1* | 10/2019 | Analytis | G01F 23/268 |
| 2019/0358387 A1* | 11/2019 | Elbadry | A61B 5/0059 |
| 2019/0365308 A1 | 12/2019 | Laing et al. | |
| 2019/0381223 A1* | 12/2019 | Culbert | A61M 1/77 |
| 2020/0022637 A1 | 1/2020 | Kurzrock et al. | |
| 2020/0064172 A1 | 2/2020 | Tabaczewski et al. | |
| 2020/0085378 A1* | 3/2020 | Burnett | A61B 5/0082 |
| 2020/0268303 A1 | 8/2020 | Oliva | |
| 2020/0289749 A1* | 9/2020 | Odashima | A61M 5/1689 |
| 2020/0405524 A1 | 12/2020 | Gill | |
| 2021/0077007 A1 | 3/2021 | Jouret et al. | |
| 2021/0299353 A1 | 9/2021 | Mannu et al. | |
| 2022/0018692 A1 | 1/2022 | Tourchak et al. | |
| 2022/0026001 A1 | 1/2022 | Cheng et al. | |
| 2022/0026261 A1 | 1/2022 | Funnell et al. | |
| 2022/0192564 A1 | 6/2022 | Kriscovich et al. | |
| 2022/0192565 A1 | 6/2022 | Cheng et al. | |
| 2022/0192566 A1 | 6/2022 | Cheng et al. | |
| 2022/0193375 A1 | 6/2022 | Rehm et al. | |
| 2022/0233120 A1 | 7/2022 | Beuret et al. | |
| 2022/0296140 A1 | 9/2022 | Nguyen et al. | |
| 2022/0386917 A1 | 12/2022 | Mann et al. | |
| 2023/0022547 A1 | 1/2023 | Cho et al. | |
| 2023/0025333 A1 | 1/2023 | Patel et al. | |
| 2023/0028966 A1 | 1/2023 | Franano | |
| 2023/0035669 A1 | 2/2023 | Raja et al. | |
| 2023/0040915 A1 | 2/2023 | Compton et al. | |
| 2023/0058553 A1 | 2/2023 | Fallows et al. | |
| 2023/0060232 A1 | 3/2023 | Patel et al. | |
| 2023/0084476 A1 | 3/2023 | Robichaud et al. | |
| 2024/0042120 A1 | 2/2024 | Cheng et al. | |
| 2024/0081708 A1 | 3/2024 | Kelly et al. | |
| 2024/0108268 A1 | 4/2024 | Woodard et al. | |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 109498013 A | 3/2019 |
| CN | 110859636 A | 3/2020 |
| CN | 112426156 A | 3/2021 |
| EP | 0342028 | 11/1989 |
| ES | 2760470 T3 | 5/2020 |
| GB | 2576743 | 3/2020 |
| JP | 849-75171 A | 7/1974 |
| JP | 854-147066 A | 11/1979 |
| JP | 858-190719 A | 11/1983 |
| JP | 860-219517 A | 11/1985 |
| JP | H02-057240 | 12/1990 |
| JP | H08-271301 A | 10/1996 |
| JP | H10-104041 A | 4/1998 |
| JP | 2007-303982 | 11/2007 |
| JP | 2008-524618 | 7/2008 |
| JP | 2009-068959 | 4/2009 |
| JP | 2010-121950 | 6/2010 |
| JP | 2010-530978 | 9/2010 |
| JP | 2012-105947 | 6/2012 |
| JP | 2012-225790 | 11/2012 |
| WO | 1981003427 A1 | 12/1981 |
| WO | 2004045410 A1 | 6/2004 |
| WO | 2013013782 A2 | 1/2013 |
| WO | 20130178742 A1 | 12/2013 |
| WO | 2014/043650 A2 | 3/2014 |
| WO | 2014108690 A1 | 7/2014 |
| WO | 2014/135856 A1 | 9/2014 |
| WO | 2014/151068 A2 | 9/2014 |
| WO | 2014145971 A2 | 9/2014 |
| WO | 201511402 A1 | 1/2015 |
| WO | 2015/105916 A1 | 7/2015 |
| WO | 2015/127390 A1 | 8/2015 |
| WO | 2015191125 A1 | 12/2015 |
| WO | 2016177901 A1 | 11/2016 |
| WO | 2017/023794 A1 | 2/2017 |
| WO | 2018156624 A1 | 8/2018 |
| WO | 2019066357 A1 | 4/2019 |
| WO | 2019/226697 A1 | 11/2019 |
| WO | 2020033752 A1 | 2/2020 |
| WO | 2020154370 A1 | 7/2020 |
| WO | 2022108589 A1 | 5/2022 |
| WO | 2022182794 A1 | 9/2022 |
| WO | 2023022895 A1 | 2/2023 |
| WO | 2023027871 A1 | 3/2023 |

OTHER PUBLICATIONS

Bard Medical, Criticore Infection Control Disposables, 3 pages, www.bardmedical.com/patienl-moniloring-,ystems/criticore®-system/criticore®-infection-control-disposables/ Jan. 30, 2015.

Bard Medical, Criticore Monitor, 11 pages, www.bardmedical.com/products/patient-monitoring-systems/ criticore®-monitor/ Jan. 30, 2015.

Bard Medical, Urine Meiers, 3 pages, www.bardmedical.com/products/urological-drainage/urine-collection/urinemeters/Jan. 30, 2015.

Biometrix, Urimetrix, 4 pages, www.biometrixmedical.com/Products/56/Urimetrix%E2%84%A2 Oct. 29, 2014.

Observe Medical, sippi, 3 pages, www.observemedical.com/products.html Oct. 29, 2014.

PCT/US19/33389 filed May 21, 2019 International Search Report and Written Opinion dated Aug. 2, 2019.

PCT/US2016/044835 filed Jul. 20, 2016 International Search Report and Written Opinion dated Dec. 16, 2016.

PCT/US2019/045787 filed Aug. 8, 2019 International Preliminary Report on Patentability dated Feb. 16, 2021.

PCT/US2019/045787 filed Aug. 8, 2019 International Search Report and Written Opinion dated Oct. 2, 2019.

U.S. Appl. No. 17/054,493, filed Nov. 10, 2020 Final Office Action dated May 31, 2022.

U.S. Appl. No. 15/748,107, filed Jan. 26, 2018 Final Office Action dated Dec. 23, 2020.

U.S. Appl. No. 15/748,107, filed Jan. 26, 2018 Final Office Action dated Feb. 7, 2022.

U.S. Appl. No. 15/748,107, filed Jan. 26, 2018 Non-Final Office Action dated Sep. 3, 2021.

U.S. Appl. No. 15/748,107, filed Jan. 26, 2018 Non-Final Office Action dated Sep. 4, 2020.

(56) References Cited

OTHER PUBLICATIONS

U.S. Appl. No. 17/054,493, filed Nov. 10, 2020 Non-Final Office Action dated Nov. 24, 2021.
U.S. Appl. No. 15/748,107, filed Jan. 26, 2018 Notice of Allowance dated Dec. 12, 2022.
U.S. Appl. No. 17/054,493, filed Nov. 10, 2020 Non-Final Office Action dated Jan. 27, 2023.
U.S. Appl. No. 17/262,080, filed Jan. 21, 2021 Non-Final Office Action dated Apr. 6, 2023.
U.S. Appl. No. 17/373,535, filed Jul. 12, 2021 Non-Final Office Action dated November 9. 2022.
U.S. Appl. No. 17/373,535, filed Jul. 12, 2021 Notice of Allowance dated Feb. 23. 2023.
PCT/US20/61367 filed Nov. 19, 2020 International Search Report and Written Opinion dated Feb. 22, 2021.
U.S. Appl. No. 17/556,907, filed Dec. 20, 2021 Restriction Requirement dated May 12, 2023.
EP 23188337.2 filed May 21, 2019 Extended European Search Report dated Dec. 4, 2023.
PCT/US2019/033389 filed Nov. 26, 2020 Extended European Search Report dated Jun. 4, 2021.
U.S. Appl. No. 17/054,493, filed Nov. 10, 2020 Notice of Allowance dated Jan. 4, 2024.
U.S. Appl. No. 17/373,546, filed Jul. 12, 2021 Non-Final Office Action dated Nov. 1, 2023.
U.S. Appl. No. 17/556,907, filed Dec. 20, 2021 Notice of Allowance dated Dec. 6, 2023.
DFree Personal—Consumer Product Brochure, 2019.
DFree Pro Brochure 2019.
Leonhäuser, D et al., "Evaluation of electrical impedance tomography for determination of urinary bladder volume: comparison with standard ultrasound methods in healthy volunteers."—BioMed Engr On-line; 17:95; 2018.
Li, R., et al., "Design of a Noninvasive Bladder Urinary Volume Monitoring System Based on Bio-Impedance."—Engineering; vol. 5; pp. 321-325; 2013.
PCT/US2022/017574 filed Feb. 23, 2022 Internation Search Report and Written Opinion dated Jun. 8, 2022.
Reichmuth, M., et al., "A Non-invasive Wearable Bioimpedance System to Wirelessly Monitor Bladder Filling."—Dep. of Health Sciences and Technology—Department of Information Technology and Electrical Engineering ETH Zurich, Zurich, Switzerland—Conference Paper, Mar. 2020.
Schlebusch, T. et al., "Bladder volume estimation from electrical impedance tomography" Physiological Measurement, Institute of Physics, Bristol, GB. vol. 35 No. 9 Aug. 20, 2014. (Aug. 20, 2014).
SECA product catalog, https://US.secashop.com/products/seca-mbca/seca-mbca-514/5141321139, last accessed Sep. 11, 2020.
U.S. Appl. No. 17/054,493, filed Nov. 10, 2020 Final Office Action dated Oct. 4, 2023.
U.S. Appl. No. 17/262,080, filed Jan. 21, 2021 Final Office Action dated Sep. 11, 2023.
U.S. Appl. No. 17/262,080, filed Jan. 21, 2021 Notice of Allowance dated Oct. 13, 2023.
U.S. Appl. No. 17/556,907, filed Dec. 20, 2021 Non-Final Office Action dated Aug. 17, 2023.
PCT/US2022/039191 filed Aug. 2, 2022 International Search Report and Written Opinion dated Dec. 5, 2022.
PCT/US2022/039746 filed Aug. 8, 2022 International Search Report and Written Opinion dated Nov. 18, 2022.
U.S. Appl. No. 17/373,546, filed Jul. 12, 2021 Notice of Allowance dated Mar. 7, 2024.
U.S. Appl. No. 17/556,931, filed Dec. 20, 2021 Non-Final Office Action dated Mar. 27, 2024.
U.S. Appl. No. 17/556,931, filed Dec. 20, 2021 Restriction Requirement dated Feb. 22, 2024.
EP 20962628.2 filed May 31, 2023 Extended European Search Report dated Apr. 20, 2024.
U.S. Appl. No. 17/373,546, filed Jul. 12, 2021 Notice of Allowance dated May 29, 2024.

\* cited by examiner

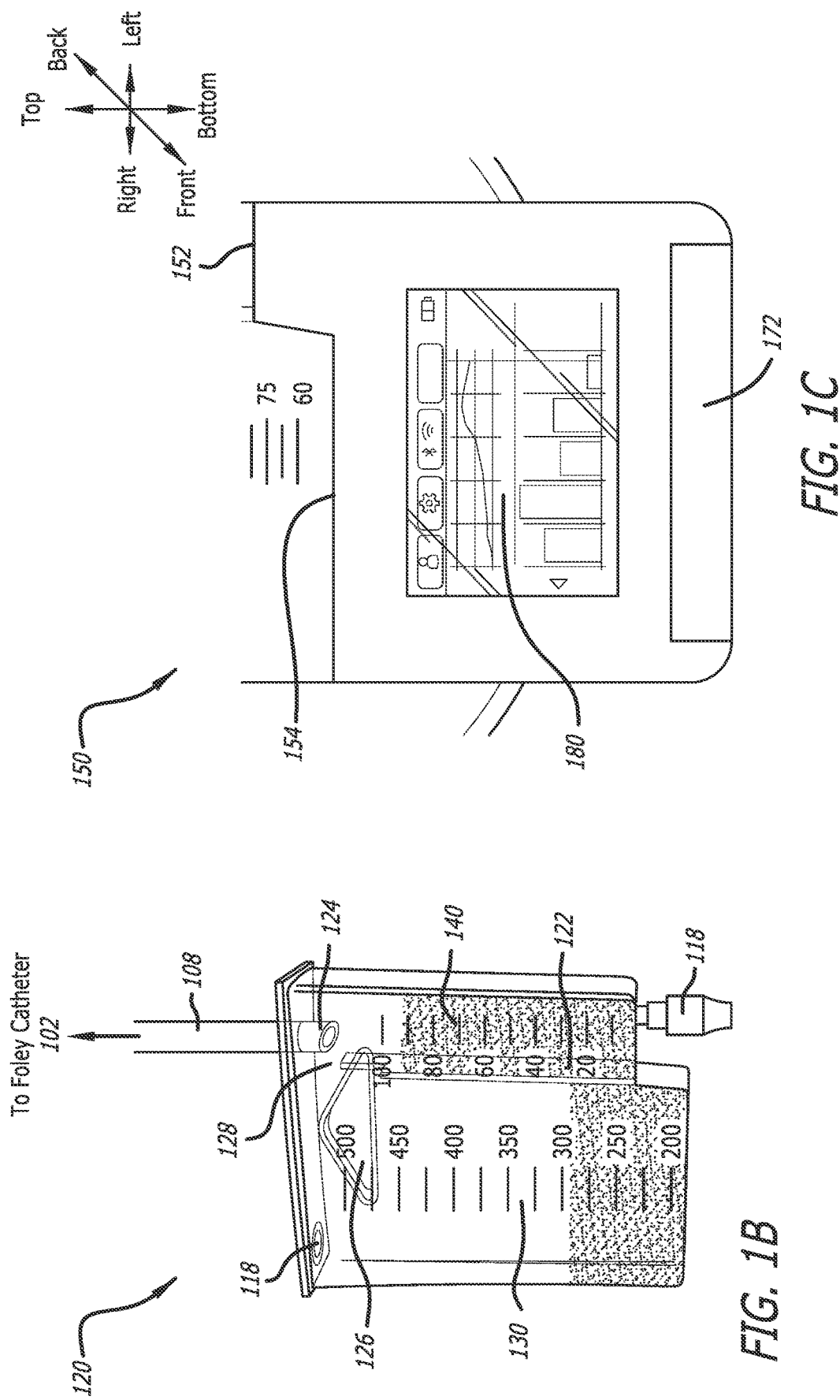

AUTOMATED FLUID OUTPUT MONITORING

PRIORITY

This application claims the benefit of priority to U.S. Provisional Application No. 63/035,567, filed Jun. 5, 2020, which is incorporated by reference in its entirety into this application.

SUMMARY

Briefly summarized, embodiments disclosed herein are directed to apparatus and methods for a fluid collection system and automated fluid flow monitoring.

In order to maintain a high accuracy of fluid flow monitoring, a fluid collection container must be checked by a clinician on a regular basis in order to record a change in fluid volume over time. This places a huge demand on the clinician in order to continually monitor a fluid flow rate. Further, due to the intermittent nature of the fluid flow, this can often lead to inaccuracies in data recording.

In a clinical situation, a patient can be catheterized but initially may not require close monitoring of fluid flow levels. However, a patient's prognosis can change or deteriorate requiring a subsequent increase in accuracy of fluid flow monitoring. Typically, the patient may have to be re-catheterized using different, more expensive, and higher accuracy measuring equipment than was previously used. However, this can lead an increased risk of introducing pathogens, discomfort for the patient, and increased overall costs.

What is needed therefore is a system that can be used in conjunction with standard fluid flow monitoring techniques that can provide increased accuracy in fluid flow monitoring while freeing up clinician resources. This system can be implemented without compromising the integrity of existing closed fluid collection systems.

Disclosed herein is a fluid collection system including, a collection container defining a first compartment and a second compartment, a transfer opening providing fluid communication between the first compartment and the second compartment, and a detection device releasably coupled to an outside surface of the collection container including, a first ultrasound transducer configured to measure a volume of a fluid disposed within the first compartment, a second ultrasound transducer configured to measure a volume of a fluid disposed within the second compartment, and an inversion sensor configured to detect an inversion event of the container.

In some embodiments, the inversion sensor includes one of a gyroscope configured to measure a tilt angle of the collection container relative to a vertical axis, or an accelerometer configured to measure a movement of the collection container in three-dimensional space. An inversion event includes one of i) rotating the collection container through a frontal plane to transfer a fluid between the first compartment and the second compartment, or ii) rotating the collection container through a medial plane to transfer a fluid between the second compartment and a collection bag. The container further includes a transfer outlet configured to provide fluid communication between the container and a collection bag. A volume of the first compartment is less than a volume of the second compartment.

In some embodiments, the detection device is configured to determine a volume of fluid disposed in the first compartment by emitting a first signal from the first transducer and determining a height of a fluid surface by measuring a time-of-flight of a first signal reflection, and determine a volume of fluid disposed in the second compartment by emitting a second signal from the second transducer and determining a height of a fluid surface by measuring a time-of-flight of a second signal reflection. The detection device is configured to determine a flow rate of fluid entering the collection container by measuring a change in volume of the first compartment, a change in volume of the second compartment, a tilt angle of the container, and an inversion event. The detection device is communicatively coupled with an external computing device.

In some embodiments, the external computing device includes one of an external monitor, laptop, computer, mobile device, smart phone, tablet, "wearable" electronic device, centralized network server, decentralized network server, a hospital intranet server, an Electronic Health Record ("EHR") system, a "cloud" based network server, or an internet server. The fluid collection system further includes a catheter in fluid communication with the first compartment, the catheter configured to drain a fluid from a cavity of a patient. The catheter includes one of an external urinary catheter, an internal urinary catheter, a Foley catheter, a balloon catheter, or a peritoneal catheter.

Also disclosed is a method of measuring a flow rate of fluid including, providing a fluid collection system, having a collection container including a first compartment in fluid communication with a second compartment, and a detection device releasably coupled to an outer surface of the collection container, directing a fluid to fill the first compartment before filling the second compartment, detecting an inversion event of the collection container, measuring a volume of fluid disposed in one of the first compartment or the second compartment, and providing a message to an external computing device including information about the volume of fluid disposed within the collection container.

In some embodiments, the external computing device includes one of an external monitor, laptop, computer, mobile device, smart phone, tablet, "wearable" electronic device, centralized network server, decentralized network server, a hospital intranet server, an Electronic Health Record ("EHR") system, a "cloud" based network server, or an internet server. The detection device includes one or more sensors configured to detect an inversion event, the one or more sensors includes one of a gyroscope configured to measure a tilt angle of the collection container relative to a vertical axis, or an accelerometer configured to measure a movement of the collection container in three-dimensional space. Detecting an inversion event includes measuring one of a surface height of fluid, a tilt angle, or a movement of the container to determine one of, i) rotating the collection container through a frontal plane to transfer a fluid between the first compartment and the second compartment, or ii) rotating the collection container through a medial plane to transfer a fluid between the second compartment and a collection bag.

In some embodiments, the container further includes a transfer outlet configured to provide fluid communication between the container and a collection bag. A volume of the first compartment is less than a volume of the second compartment. Measuring a volume of fluid disposed in one of the first compartment or the second compartment includes emitting a signal from a transducer and determining a height of a fluid surface by measuring a time-of-flight of a signal reflection. The detection device is configured to determine a flow rate of fluid entering the collection container by measuring a change in fluid volume disposed within the collection container a tilt angle of the container, and an inversion event.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1B shows a perspective view of a collection container, in accordance with embodiments disclosed herein.

FIG. 1C shows a front view of a detection device, in accordance with embodiments disclosed herein.

DESCRIPTION

Figure 1A:
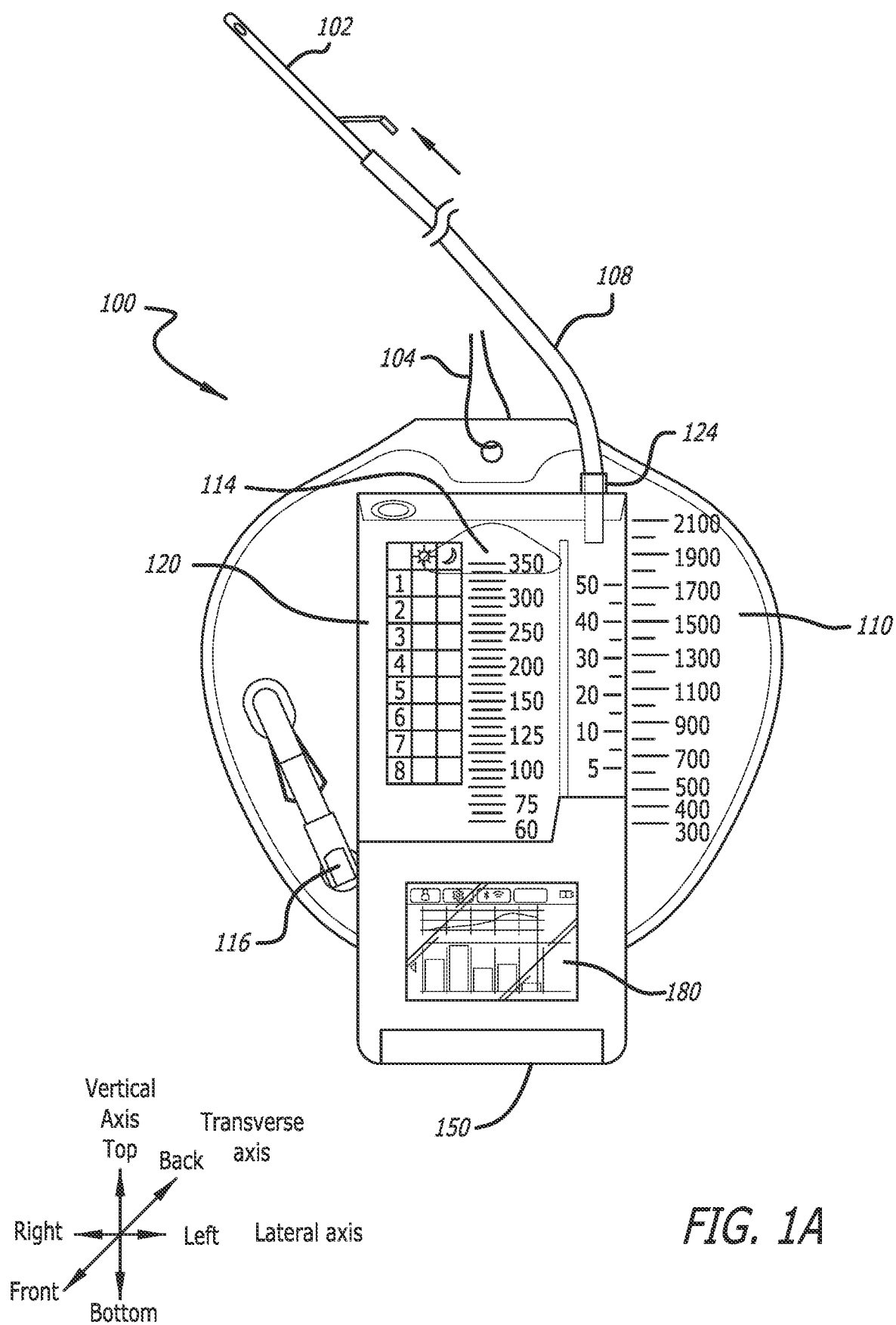
FIG. 1A shows a perspective view of an exemplary fluid collection system including a collection container and a detection device, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Terminology

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

Figure 4C:
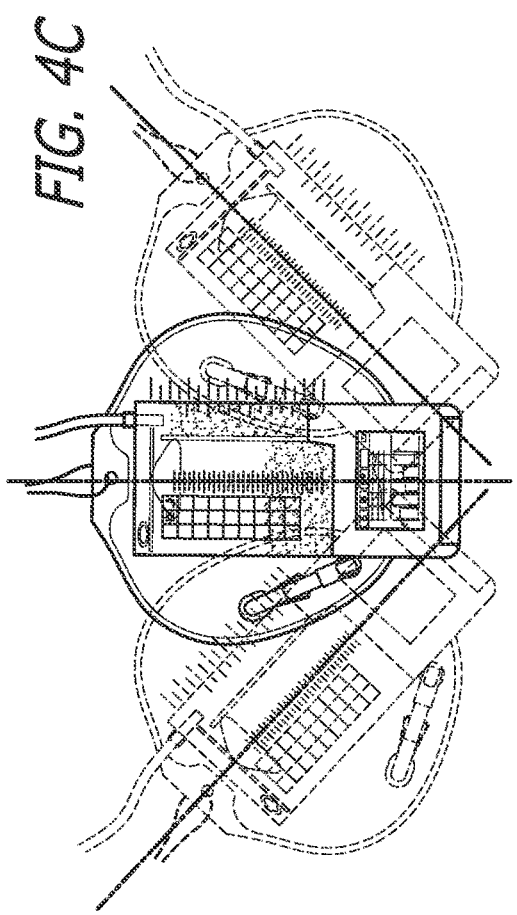
FIG. 4C shows exemplary tilt events of a collection container, in accordance with embodiments disclosed herein.
Figure 4D:
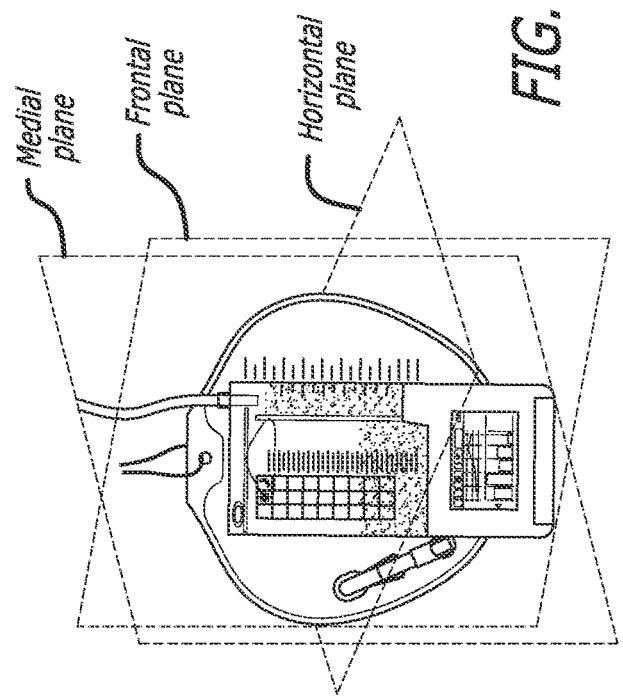
FIG. 4D shows exemplary orientation planes of a collection container, in accordance with embodiments disclosed herein.
Figure 4A:
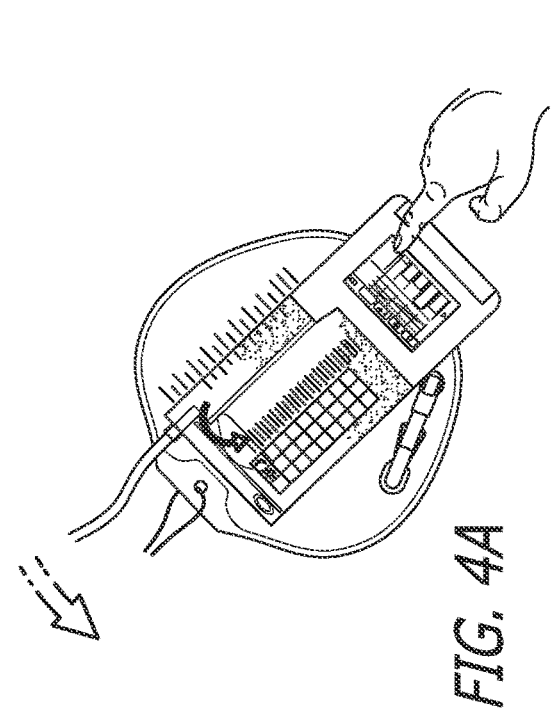
FIGS. 4A-4B show exemplary inversion events of a collection container, in accordance with embodiments disclosed herein.

Labels such as "left," "right," "upper", "lower," "top," "bottom," "front," "back," and the like are used for convenience and are not intended to imply, for example, any particular fixed location, orientation, or direction. Instead, such labels are used to reflect, for example, relative location, orientation, or directions. To assist in the description of embodiments described herein, the "top," "bottom," "left," "right," "front" and "back" directions are in reference to the orientation of the device as shown in FIGS. 1, 4D. A vertical axis extends between a top direction and a bottom direction. A lateral axis extends horizontally between a left direction and a right direction, substantially normal to the vertical axis. A transverse axis extends horizontally between a front direction and a back direction, substantially normal to both the vertical and lateral axes. A horizontal plane is defined by the lateral and transverse axes. A median plane is defined by the vertical and transverse axes. A frontal plane is defined by the vertical and lateral axes.

Unless defined otherwise, all technical and scientific terms used herein have the same meaning as commonly understood by those of ordinary skill in the art.

Fluid Collection System

FIGS. 1A-1C show details of an exemplary fluid collection system ("system") 100, in accordance with embodiments disclosed herein. The system 100 generally includes a collection container ("container") 120, and a detection device 150. The detection device 150 can be coupled to an outside surface of the collection container 120 and can be configured to detect a volume of fluid disposed therein. The collection container 120 can be in fluid communication with a catheter 102 and drainage tubing 108 configured to drain a fluid from a cavity of a body. An outlet of the container 120 can be in fluid communication with a collection bag 110 configured to receive fluid that is emptied from the container 120. Optionally fluid from the container 120 can be emptied and directly disposed of. The catheter 102 can be an internal catheter or an external catheter. Exemplary catheters can include external urinary catheter, internal urinary catheter, Foley catheter, balloon catheter, peritoneal catheters, or the like. Exemplary fluids collected can include urine, blood, peritoneal fluid, interstitial fluid, or the like. In an embodiment, the catheter 102 can be a Foley catheter configured to drain a fluid, e.g. urine, from a bladder of a patient.

The collection bag 110 can be a flexible or rigid receptacle and can define a front surface and a back surface. The collection bag 110 can include an inlet 114 disposed proximate a top edge, and drainage outlet 116 disposed proximate a bottom edge. Optionally the drainage outlet 116 can include one or more valves, connectors, or the like to facilitate emptying fluid from the collection bag 110 while mitigating the introduction of pathogens and the like to the closed fluid collection system. The fluid collection system 100 can further include a hook 104, or similar attachment means to suspend the system 100 in a substantially vertical orientation, as shown in FIG. 1A.

The collection container 120 can be coupled to the collection bag, e.g. a front surface of the collection bag 110, and can be in fluid communication therewith. As shown in FIG. 1B, the collection container 120 can be a substantially rigid structure and can include an inlet 124, a transfer outlet 126, and optionally one or more drainage outlets 118, sampling ports, or the like. The transfer outlet 126 can be disposed proximate to top surface of the container 120 and be fluidly coupled with an inlet 114 of the collection bag 110 to allow fluid to be transferred between the container 120 and the collection bag 110. The drainage outlet 118 can include one or more valves, connectors, or the like to facilitate emptying fluid from the container 120 while mitigating the introduction of pathogens and the like to the closed fluid collection system. In an embodiment, the transfer outlet 126 can also include one or more valves, connectors, or the like to facilitate emptying and disposing of fluid from the collection system 100.

The inlet 124 of the container 120 can be configured to engage the drainage tubing 108 and provide fluid communication between the tubing 108 and the container 120. Optionally the inlet 124 can include a connector. Exemplary connectors can include Foley connectors, interference fit connectors, spin nut, luer locks, or the like.

In an embodiment, the collection container 120 can define one or more fluid collection compartments. For example, the container 120 can include a partition 122 that divides the container 120 into a standard accuracy graduated compartment ("SAGC") 130 and a high accuracy graduated compartment ("HAGC") 140. Each of the SAGC 130 and the HAGC 140 can define a substantially rectangular horizontal cross-sectional shape. However other horizontal cross-sectional shapes are also contemplated. In an embodiment, a volume defined by the SAGC 130 can be larger than a volume defined by the HAGC 140. In an embodiment, the SAGC 130 defines a volume of substantially 300 ml and the HAGC 140 defines a volume of substantially 50 ml. However, it will be appreciated that greater or lesser volumes for each of the SAGC 130 and the HAGC 140 are also contemplated. Further, it will be appreciated that different ratios of volumes between the SAGC 130 and the HAGC 140 are also contemplated.

The inlet 124 can be aligned such that any fluid entering the container from the catheter 102 is directed into the HAGC 140. As shown, the inlet 124 is disposed in a top surface of the container 120. However, it will be appreciated that the inlet 124 can also be disposed in a side surface or a lower surface of the container without departing from the spirit of the invention.

As noted, fluid entering the container 120 is directed to the HAGC 140. As the HAGC 140 defines a relatively smaller cross-sectional area, an increase in fluid volume within the HAGC 140 defines a greater vertical change in fluid surface level than that of a similar volume increase in the SAGC 130. As such, the HAGC 140 can indicate a greater accuracy in fluid volume changes, i.e. fluid flow rate, than the SAGC 130.

The container 120 can further include a transfer opening 128 disposed proximate an upper side of the container 120 and provides fluid communication between the SAGC 130 and the HAGC 140. When the HAGC 140 is full, the fluid can be transferred from the HAGC 140 to the SAGC 130. Advantageously, the transfer opening 128 is configured such that if fluid continues to enter the container after the HAGC 140 has reached capacity, the fluid can flow into the SAGC 130 and a total volume of fluid can still be recorded. Transferring fluid from the HAGC 140 to the SAGC 130 can allow a clinician to continue to monitor a fluid flow rate with a high level of accuracy.

As shown in FIGS. 4A-4D, in an embodiment, transferring fluid between the HAGC 140 to the SAGC 130, or between the container 120 and the collection bag 110 can be termed an "inversion event." An inversion event can include rotating the container 120 laterally through a frontal plane (FIG. 4A) or transversely through a medial plane (FIG. 4B) such that at least a portion of fluid can transfer between the HAGC 140 and the SAGC 130, or between the container 120 as a whole, and the collection bag 110. An inversion event can differ from a "tilt" event, in which the container 120 is tilted relative to a vertical axis but no fluid is transferred. As will be appreciated, an absolute angle at which a tilt even is differentiated from an inversion event can vary depending on the vertical level of the fluid surface within the compartments of the container 120, as discussed in more detail herein.

Detection device

As shown in FIG. 1C, in an embodiment, a detection device 150 can be releasably coupled to an outer surface of a collection container 120. The detection device 150 can include one or more sensors configured to detect one or more parameters. For example the detection device 150 can determine a fluid volume disposed within the container 120, a tilt angle, movement of the container 120, body temperature, or the like. Advantageously, the detection device 150 can be coupled to the collection container 120 without having to re-catheterize the patient or compromise the closed fluid collection system 100.

The detection device 150 can define a substantially cuboid shape, defining a top surface, bottom surface, front surface, back surface, left surface and a right surface. However, it will be appreciated that other suitable three-dimensional shapes are also contemplated. In an embodiment, a top surface of the detection device 150 can be releasably coupled to a bottom surface of the container 120 using one or more attachment mechanisms 174 (FIG. 5C). Exemplary attachment mechanisms can include snap-fit, interference fit, press-fit, clips or lugs and detents, thread bolts and nuts, hook-and-loop attachments, magnets, adhesives, combinations thereof, or the like. Corresponding attachment mechanisms 174 can be disposed on a bottom surface of the container 120. In an embodiment, the detection device can include a handle 172 disposed proximate a bottom surface to facilitate tipping and emptying the container 120/detection device 150 assembly. (e.g. FIG. 4B).

In an embodiment, the detection device can include a control interface 180. The control interface 180 can include one or more physical push buttons, switches, dials, sliders, screens, touchscreens, lights, LED lights, speakers, combinations or the like configured to display information and receive inputs from a user. As shown, the control interface 180 is disposed on a front surface of the detection device 150, however, it will be appreciated that the control interface 180, or portions thereof, can be disposed on any of the surfaces of the detection device 150.

Figure 2A:
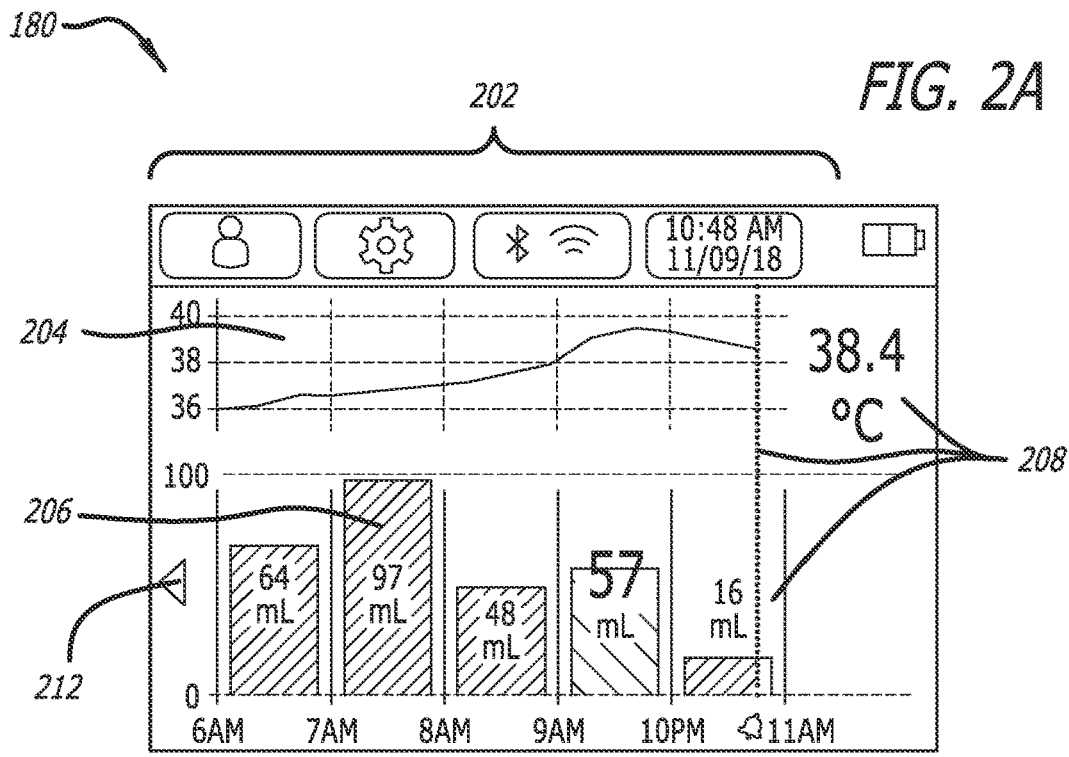
FIGS. 2A-2B show exemplary screenshots of the detection device of FIG. 1A, in accordance with embodiments disclosed herein.
Figure 2B:
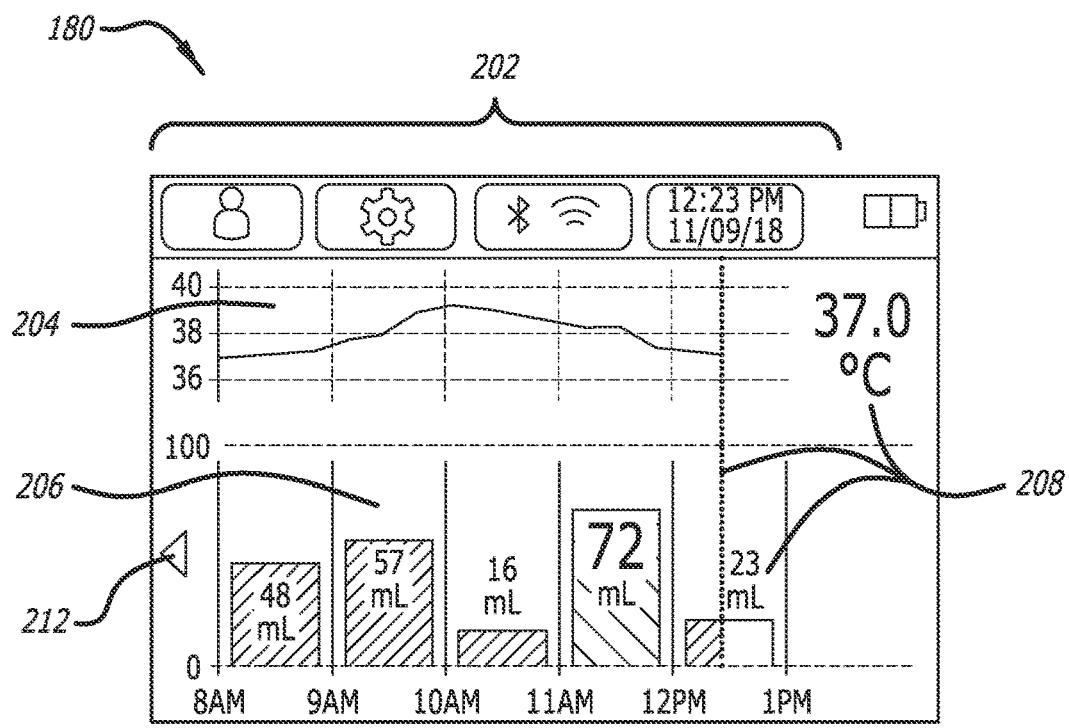

FIGS. 2A-2B show exemplary screenshots of the control interface 180. In an embodiment, the control interface 180 can be a touchscreen displaying one or more charts, graphics, icons, selection buttons and the like. The interface 180 can include one or more selection buttons 202 allowing a user to access additional information or settings, e.g. patient information, configuration settings, communication settings, synchronization events, date/time, battery life, alarms, notifications, combinations thereof, or the like.

The interface 180 can include one or more charts depicting information detected by one or more sensors of the detection device 150, e.g. a body temperature chart 204, a fluid flow chart 206, combinations thereof or the like. Exemplary sensors 320 can include temperature sensors, fluid volume sensors, gyroscopic sensors, accelerometers, and the like, as described in more detail herein (FIG. 3).

For example, a body temperature chart 204 can show a change in internal body temperature over time and can be shown as a line chart. A fluid flow chart 206 can show a volume of fluid received by the container 120, or individual compartments 130, 140, within a given period to time and can be shown as a bar chart. It will be appreciated however that these are exemplary and the information (temperature, fluid volume, fluid flow, etc.) over time can be displayed by a variety of icons, graphics, charts, etc. without limitation. Further, while a given time period is shown in one hour increments it will be appreciated that a clinician can select lesser or greater time increments. The interface 180 can further indicate a current measurement 208 of temperature, fluid volume, or the like. As shown by comparing FIGS. 2A-2B, the interface 180 can display the current measurements 208 with a scrolling chart indicating historical data. In an embodiment, the interface can further include a scroll button 212 configured to show additional historical data.

A clinician can use the interface 180 to enter further information, or adjust the information displayed, e.g. modifying a time interval, units displayed, data input, or the like. In an embodiment, the detection device 150 can store the information locally on the detection device 150, can be communicated to/from one or more external computing devices, or combinations thereof.

Figure 3:
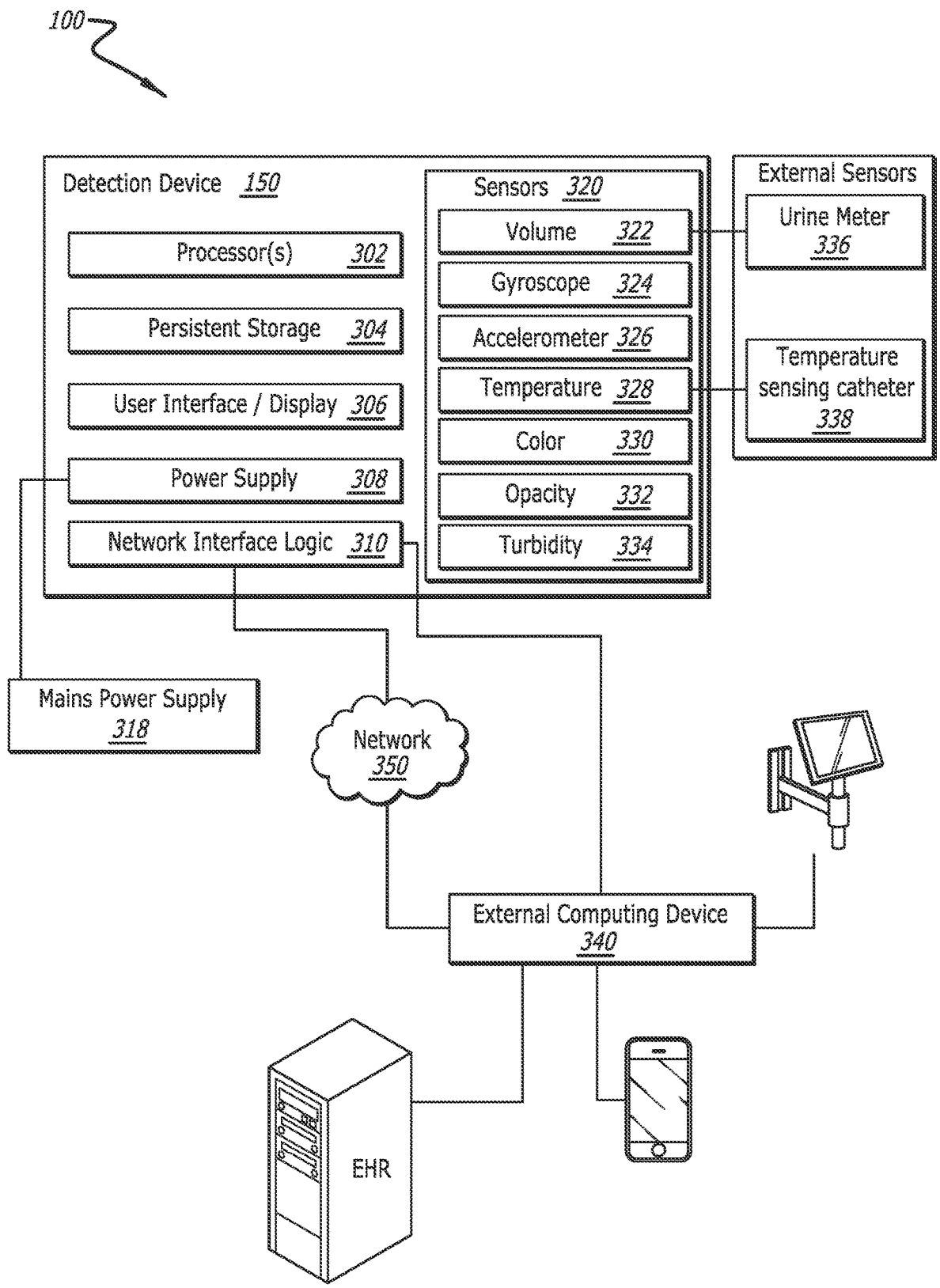
FIG. 3 shows a schematic view of an exemplary environment of use for the detection device of FIG. 1A, in accordance with embodiments disclosed herein.

FIG. 3. shows a schematic view of the detection device 150 in an exemplary environment of use. In an embodiment, the detection device 150 can include one or more processor(s) 302, persistent storage 304 (e.g. hard drive, flash drive, solid state disc, or the like), user interface or display 306 (e.g. touch screen user interface 180), a power supply 308 (e.g. battery, mains power 318), a network interface logic 310, or sensors 320.

Exemplary sensors 320 can include, but not limited to, fluid volume sensors 322 (e.g. ultrasound transducer 152, 154), tilt or inversion sensors, e.g. gyroscope 324, accelerometer 326, temperature sensor 328 (e.g. body temperature, fluid temperature), optical sensors, e.g. to measure color 330, opacity 332, turbidity 334, of the fluid, combinations thereof, or the like, as discussed in more detail herein. Optionally, one or more of the sensors 320 can be communicatively coupled with additional external sensors. For example, the fluid volume sensors 332 can be communicatively coupled with additional fluid volume sensor(s) 336 disposed within the fluid collection system 100. Similarly, the temperature sensor 328 can be coupled with a temperature sensing Foley catheter 338, or the like, as described herein.

The detection device 150 can be communicatively coupled with one or more external computing devices 340, or with a centralized or decentralize network 350, or combinations thereof. The detection device 150 can include a network interface logic 310 that can provide wired or wireless communication with the external computing device 340 or network 350. Exemplary wireless communication can include Bluetooth, Wifi, Near Field Communication (NFC), cellular Global System for Mobile Communication ("GSM"), combinations thereof, or the like. Exemplary external devices can include external monitors, laptop, computers, mobile devices, smart phones, tablets, "wearable" electronic devices, centralized or decentralized networks, hospital intranet server, Electronic Health Record ("EHR") systems, "cloud" based networks, internet, combinations thereof, or the like.

In an embodiment, information detected by the sensors 320 of the detection device 150 can be stored and analyzed locally or can be communicated through messages with one or more external devices to be stored and analyzed remotely. In an embodiment, the detection device 150 can determine when to provide an alert to a clinician. The alert can be provided directly from the detection device 150 as a visual, audible, or tactile alert, or can be communicated to one or more external computing devices 340 or network 350.

In an embodiment, the detection device 150 can include an internal power supply 308, e.g. a rechargeable battery, or be coupled to an external power source, e.g. mains power 318. Advantageously, this allows the detection device 150 to continue to operate when the patient is being transported, or does not have access to an external power source. In an embodiment, the internal power source 308 is configured to provide sufficient power for the detection device to operate for at least 48 hours. However, it will be appreciated that greater or lesser operation times are also contemplated.

In an embodiment, the detection device 150 includes a temperature sensor 328. The temperature sensor can measure a temperature of fluid in the container 150, of fluid entering the container at the inlet 124, or can be communicatively coupled, either wired or wirelessly, with a temperature sensing Foley catheter disposed within the body cavity to measure an internal body temperature of the patient, or combinations thereof. Exemplary temperature sensing catheters are described in WO 2014/151068, which is incorporated by reference in its entirety herein.

In an embodiment, the detection device 150 can include one or more volume sensors configured to measure a volume of fluid disposed in the container 120. In an embodiment, the detection device 150 includes a first volume sensor, e.g. a first transducer 152, configured to measure a fluid volume within a first compartment, e.g. HAGC 140, and a second volume sensor, e.g. a second transducer 154, configured to measure a fluid volume within a second compartment, e.g. SAGC 130. Advantageously, the first transducer 152 and the second transducer 154 can determine a fluid volume independently of each other. Further, the rate, or time interval between volume measurements can be adjusted independently, depending on the level of accuracy required.

In an embodiment, the first transducer 152 and the second transducer 154 can be disposed in a top surface of the detection device 150 and configured to engage a bottom surface of the HAGC 140 and the SAGC 130 respectively. The first transducer 152 or the second transducer 154 can include one or more biasing members to ensure a suitable conductive fit between the transducer 152, 154, and the compartment 130, 140 depending on the modality employed by the transducer 152, 154. For example, one of the first transducer 152 or the second transducer 154 can be an ultrasonic transducer. A biasing member can be configured to bias the transducer against a surface of the container 120 to ensure suitable acoustic conductivity between the transducers and the compartments. In an embodiment, the transducer can further include one more conductive couplings, e.g. rubber grommets, acoustic gels, or the like, disposed between the transducer and the compartment, to ensure suitable acoustic conductivity therebetween.

Advantageously, one of the first transducer 152 or the second transducer 154 can be coupled with an outer surface of the container and configured to detect a volume of fluid disposed therein without compromising the integrity of the closed system. This mitigates the introduction of pathogens and prevents the discomfort and expense of re-catheterizing the patient with specialized equipment.

In an embodiment, the first transducer 152 or the second transducer 154 can employ various modalities, including acoustic, capacitance, electro-resistance electromagnetic (EM), radio frequency (RF), microwave, combinations thereof, or the like. In an embodiment, the first transducer 152 or the second transducer 154 can employ the same modality. In an embodiment, the first transducer 152 or the second transducer 154 can employ different modalities. As such, the detection device 150, container 120, or combinations thereof can include suitable connection structures to ensure efficient connectivity between the transducers 152, 154 of the detection device 150 and the compartments 130, 140 depending on the modality used.

In an embodiment, one of the first transducer 152 or the second transducer 154 can be an ultrasonic transducer that emits an acoustic pulse vertically, through the fluid, and determines a time-of-flight of a return signal reflected off of the fluid surface. The detection device 150 can then calculate a vertical height of the fluid disposed within the compartment 130 140 of the container 120. The detection device 120 can then determine a volume of fluid disposed therein by combining the time-of-flight measurements with predetermined cross-sectional area of the compartment.

In an embodiment, the second transducer 152 aligns with the HAGC 140 and is configured to measure a volume of fluid disposed therein. For example, the second transducer 154 can be an ultrasonic transducer that emits an acoustic pulse vertically, through the fluid, and determines a time-of-flight of a return signal reflected off of the fluid surface. The detection device 150 can then a volume of fluid disposed therein. It will be appreciated that the cross sectional area of both the SAGC 130 and the HAGC 140 can be predetermined since the container 120 is formed of a rigid material, the detection device can then combine the time-of-flight measurements with the cross-sectional area to determine a fluid volume. In an embodiment, details of the container 120 can be entered to the detection device 150 by a clinician.

Advantageously, the modality of the transducer 152, 154 is configured to pass through a bottom wall of the container 120. As such, the detection device 150 can be coupled to an outer surface of the container 120 without the need for the sensors to directly contact the fluid being measured. Further, the detection device 150 can be coupled to a container 120 that is already in use without the need to compromise the sterility of a closed fluid collection system, nor having to re-catheterize the patient with specialized equipment.

In an embodiment, the detection device 150 can include one or more sensors configured to detect an inversion event of the container. In an embodiment, the inversion sensor can include one of a gyroscope sensor or an accelerometer sensor configured to detect an orientation or movement of the detection device 150, or combinations thereof. For example the gyroscope can detect a tilt angle and an accelerometer can detect a speed of linear or rotational movement in three dimensional space. As shown in FIG. 4C, in an embodiment, the detection device 150 can determine if the container 120 is tilted relative to the vertical axis. The tilt angle can affect the surface level height and the detection device 150 which in turn can affect the fluid volume calculations. As such, the detection device 150 can include algorithms, predetermined rule sets, machine learning, Artificial Intelligence (A.I.), neural networks, combinations thereof, or the like, to compensate for any tilt relative to the vertical axis when calculating the fluid volume. As used herein, a "tilt" event is where the detection device 150/container 120 assembly is rotated relative to the vertical axis but there is no fluid transfer between compartments or between the container 120/collection bag 110 assembly.

In an embodiment, the detection device 150 can received information from the gyroscope, accelerometer, and the volume sensor(s), e.g. transducers 152, 154 to differentiate between a tilt event or an inversion event, where fluid is transferred to/from the SAGC 130, HAGC 140, container 120, collection bag 110, or combinations thereof. To note, an inversion event can either be intentional or unintentional.

As will be appreciated, an absolute angle that differentiates between a tilt event (FIG. 4C) and an inversion event (FIGS. 4A, 4B) can depend on the volume of fluid, and therefore a vertical height of a fluid surface, within the compartments of the container 120. For example, a larger volume of fluid within the HAGC 140 will require a small angle tilt for an inversion event to occur compared with a smaller volume of fluid.

As such, the detection device 150 can determine a volume of fluid within the SAGC 130, HAGC 140, a tilt angle of the container 120 and a direction and speed of movement of the container 120 to determine if an inversion event has occurred. When an inversion event has occurred, this information can be communicated with one or more external computing devices 340, for example to store the event in the patients Electronic Health Record (EHR) and/or notify a clinician. The inversion event can be further confirmed by a comparison of volume changes before and after the inversion event.

By way of an example, a fluid volume within the HAGC 140 can be 45 ml and the fluid volume within the SAGC 130 can be 100 ml where a maximum fluid capacity of the HAGC 140 and the SAGC 130 can be 50 ml and 300 ml. The detection device 150 can determine that a fluid within HAGC 140 is reaching a maximum capacity and can send a message to an external computing device 340 to notify a clinician. The container 120 can then be tilted sufficiently to cause an inversion event where a fluid is transferred from the HAGC 140 to the SAGC 130. The detection device 150 can determine that an inversion event has occurred and can confirm as such by a decrease in fluid volume in the HAGC 140 and an increase in fluid volume in the SAGC 130. The detection device 150 can send one or more messages to an external computing device to indicate the inversion event and changes in fluid volumes. Similarly, the detection device 150 can determine an inversion event between the container 120 and the collection bag 110 based on the angle of tilt, direction of movement and drop in total volume of the fluid within the container 120 as fluid is transferred out of the container 120 and into the collection bag 110. The detection device 150 can then communicated the information about the tilt event, inversion event, a change in fluid volume to one or more external computing devices, and/or determine when to alert a clinician.

In an embodiment, the fluid collection system 100 can further include or be coupled to support structures configured to automatically perform an inversion event either between compartments 130, 140, or between the container 120 and the collection bag 110. Further, the detection device 150 can be communicatively coupled to the auto-empty structures to initiate automatic emptying of the compartments/containers.

In an embodiment, the fluid collection system 100 can further include a suction pump coupled directly, or indirectly, to the drainage tubing 108 and configured to draw the fluid through the drainage tube into the collection container 120. Advantageously this can ensure all fluid is drained from the catheter and drainage tube to ensure accurate fluid flow measurements.

Exemplary Method of Use

Figure 5C:
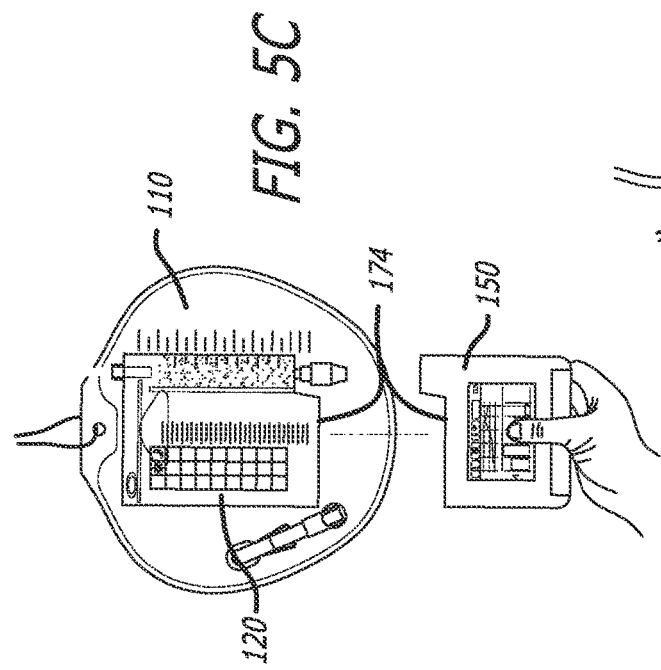
FIGS. 5A-5G show an exemplary method of use for a fluid collection system, in accordance with embodiments disclosed herein.
Figure 5D:
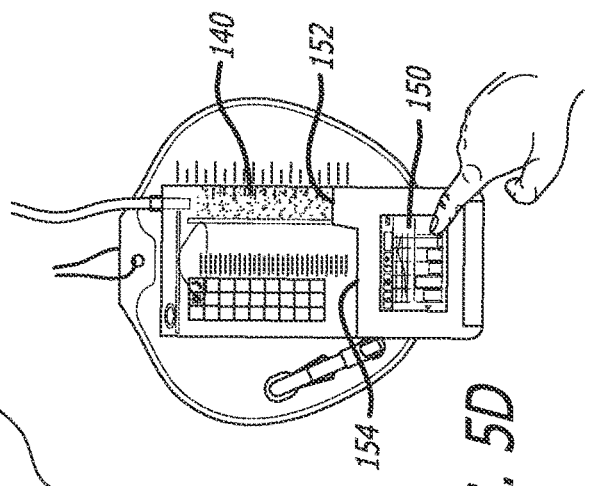
Figure 5A:
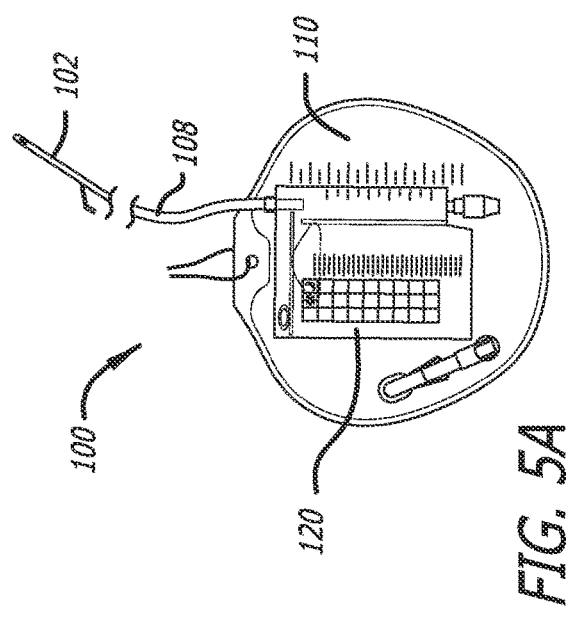
Figure 5B:
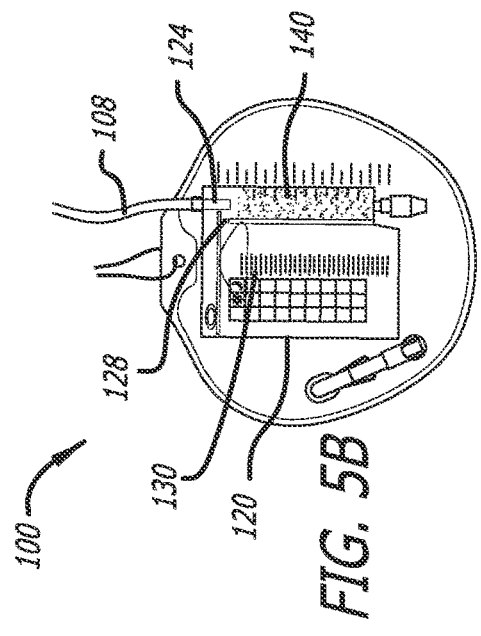

In an exemplary method of use, as shown in FIG. 5A, a fluid collection system 100 including a container 120 can be used to collect a fluid from a drainage tube 108 that is in fluid communication with a catheter 102. Optionally, the container 120 can be in fluid communication with a collection bag 110. The catheter 102, tubing 108, container 120 and collection bag 110 can provide a closed system to mitigate the introduction of pathogens or similar catheter-associated urinary tract infection (CAUTI) causing agents or pathogens.

Figure 4B:
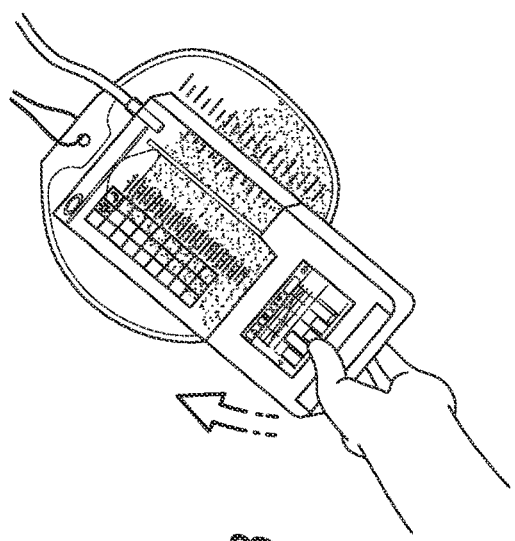

As shown in FIG. 4B, a fluid drained from the catheter 102 and tubing 108 can enter the container by way of the inlet 124. The inlet 124 can be configured to direct the fluid into a first compartment of the container 120, e.g. a HAGC 140. Initially there may be little or no need to monitor a fluid flow into the container 120. Alternatively fluid flow can be monitored manually whereby an amount of fluid entering the HAGC 140 can be monitored and recorded at a given time interval using the graduated markings before being emptied into the SAGC 130. Transferring fluid from the HAGC 140 to the SAGC 130 can be achieved by rotating the container through a frontal plane.

In like manner a fluid flow into the SAGC 130 can be monitored and recorded before emptying the fluid into the collection bag 110 by rotating the container through the medial plane. As will be appreciated monitoring a fluid flow in the HAGC 140 requires more frequent attention from a clinician, given the smaller volume. However, a higher degree of accuracy in fluid flow rates can be obtained. If such accuracy in fluid flow rates are not required, fluid can overflow from the HAGC 140 into the SAGC 130 by way of the transfer opening 128. This demands less frequent monitoring from a clinician.

For a variety of reasons, a prognosis of the catheterized patient can change and require more close monitoring of fluid flow, or other parameters. Typically the patient may have to be re-catheterized with a more specialized fluid collection system. However, in the present invention, as shown in FIG. 5C, a detection device 150 can be coupled to an outside surface of the existing collection container 120. In an embodiment, the detection device 150 can be releasably coupled to a lower surface of the container 120 with one or more clips, or similar attachment mechanisms. Advantageously, the detection device 150 can be coupled with the container 120 without having to compromise the integrity of the closed fluid collection system nor, re-catheterize the patient. Similarly, the detection device 150 can be removed from container 150 without having to disturb the catheter 102 or the closed collection system.

Figure 5E:
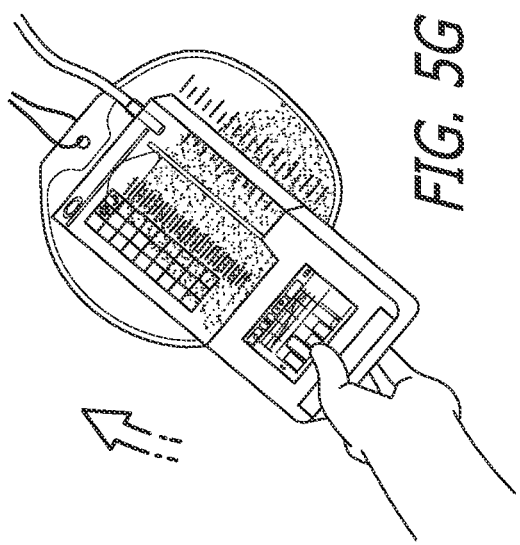

As shown in FIGS. 5D-5E, the detection device 150 can include one or more sensors configured to detect one or more parameters. For example, a first ultrasonic transducer 152, disposed in an upper surface of the detection device 150 can emit a first acoustic signal through the wall of the container 120 and upwards through the volume of fluid disposed within HAGC 140. The signal can be reflected off of the fluid surface and the reflected signal can be detected by the transducer 152. The detection device 150 can determine a time-of-flight between the emitted signal and the reflected signal, which can indicate a vertical height of the fluid volume and, together with the predetermined cross-sectional area of the HAGC 140, a volume of fluid can be calculated. In like manner, a second ultrasonic transducer 154 can determine a volume of fluid disposed within the SAGC 130. Advantageously, the detection device 150 can immediately determine a volume of fluid within the container 120 without requiring any historical fluid flow information. In an embodiment, the initial volume can be adjusted by the clinician using the control interface 180 depending, for example, if any fluid has been drained from the container 120 to the collection bag 110. As shown in FIG. 5E, in an embodiment, the detection device 150 can be coupled with a temperature sensing Foley catheter configured to detect an internal body temperature of the patient.

In an embodiment, the fluid collection system 100 can be suspended from a hook 104, which can bias the fluid collection system 100 to a vertical orientation. However, as shown for example in FIG. 4C, the collection system 100 can be tilted, either intentionally or unintentionally which can affect the surface level height and time-of-flight measurements. In an embodiment, the detection device 150 can include a gyroscope, an accelerometer, or combinations thereof to determine a tilt angle or movement of the collection container 120 which can affect a vertical height of a fluid surface. As such, the detection device 150 can detect and compensate for the tilt angle when measuring a fluid volume within the container 120.

In an embodiment, the detection device 150 can determine that a volume of fluid within the HAGC 140 is approaching the maximum volume of fluid that the HAGC 140 can hold. The detection device 150 can provide an alert to indicate the HAGC 140 requires emptying in order to continue a high accuracy flow monitoring. In an embodiment, the alert can be a visual, audible, tactile alert, or combinations thereof, provided by the detection device 150, and configured to alert a clinician proximate the detection device that the HAGC 140 can be emptied. In an embodiment, the detection device 150 can provide a message to one or more external computing devices to notify a clinician that the HAGC 140 requires emptying. Similarly, the detection device 150 can determine that a volume of fluid within the SAGC 130, or container 120 as a whole, is approaching the maximum volume and provide an alert, as described herein.

Advantageously, the detection device 150 can alert the clinician only when the collection device requires attention and increases efficiency of the clinicians' time and resources from checking the collection system too often. Similarly, the alerts prevent the collection system from over flowing and losing fluid flow data by continuing to fill after the HAGC 140 and/or SAGC 130 are full.

Figure 5F:
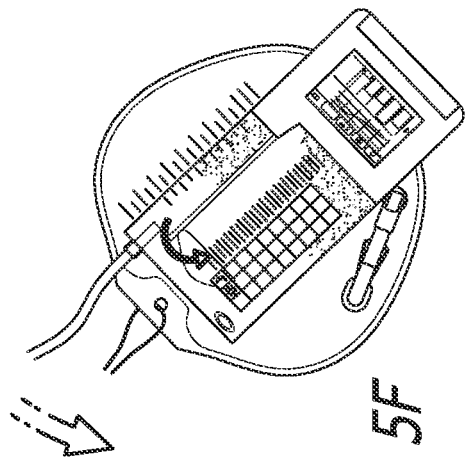
Figure 5G:
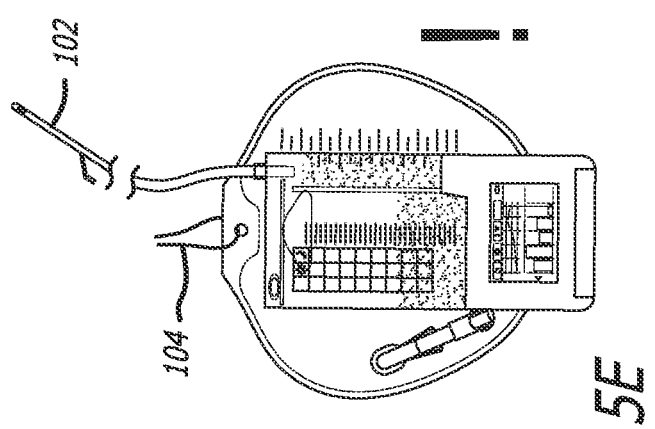

As shown in FIG. 5F, in an embodiment, fluid in the HAGC 140 can be emptied into the SAGC 130 by rotating the container 120 through the frontal plane, termed an "inversion event." Similarly, as shown in FIG. 5G, an "inversion event" can also include emptying a fluid disposed in the SAGC 130, or the container 120 as a whole, into the collection bag 110 by rotating the container 120 through the medial plane. The detection device 150 can determine a fluid surface height, a tilt angle, and a lateral or rotational movement of the container 120 from the volume sensors, gyroscope, accelerometer, or combinations thereof to determine when an inversion event has occurred and a portion of fluid has been transferred. The detection device 150 can then record these events and include the changes in relative fluid volume when calculating fluid flow rates over time.

Advantageously, when an inversion event occurs the detection device 150 automatically records such events and can reset the volume measurements and flow rates without a clinician having to adjust any settings. Instead the clinician simply has to invert the container. This significantly simplifies and reduces the time taken to reset the collection device 100. Further, less training is required to reset the device 150 allowing other personnel to reset the system 100. Additionally, the inversion event can be automatically detected and a message can be sent to an external computing device to record the event and alert a clinician. For example, a support personnel can perform the inversion event and the detection device 150 can alert the primary clinician in charge of the patient that the inversion event has occurred, even when they are at a remote location. Fluid entering the container 120 can then continue to fill the HAGC 140 and the detection device 150 can continue to determine with high resolution accuracy a flow rate.

As will be appreciated, a clinician can adjust settings to provide an alert when the fluid volume within the container 120, or compartments thereof, is at less than 100% capacity. This can provide a clinician, or a supporting staff, sufficient time to return to the system 100 and perform an inversion event. This prevents the compartments 130, 140 or container 120 over flowing and allows the detection device 150 to continue to measure fluid flow at a high accuracy.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A fluid collection system, comprising:
   a catheter;
   a drainage tube;
   a collection container defining a first compartment and a second compartment, a transfer opening providing fluid communication between the first compartment and the second compartment;
   a collection bag, wherein the catheter, the drainage tube, the collection container, and the collection bag define a closed liquid collection system; and
   a detection device releasably coupled to an outside surface of the collection container and configured to measure a volume of liquid within the collection container without compromising an integrity of the closed liquid collection system, and comprising:
   a first ultrasound transducer configured to measure a first volume of a liquid disposed within the first compartment;

a second ultrasound transducer configured to measure a second volume of the liquid disposed within the second compartment; and an inversion sensor configured to detect an inversion event of the collection container.

2. The fluid collection system according to claim 1, wherein the inversion sensor includes one of a gyroscope configured to measure a tilt angle of the collection container relative to a vertical axis, or an accelerometer configured to measure a movement of the collection container in three-dimensional space.

3. The fluid collection system according to claim 1, wherein the inversion event includes one of:
   i) rotating the collection container through a frontal plane to transfer the liquid between the first compartment and the second compartment; or
   ii) rotating the collection container through a medial plane to transfer the liquid between the second compartment and the collection bag.

4. The fluid collection system according to claim 1, wherein the collection container further includes a transfer outlet configured to provide fluid communication between the collection container and the collection bag.

5. The fluid collection system according to claim 1, wherein the first volume of the first compartment is less than the second volume of the second compartment.

6. The fluid collection system according to claim 1, wherein the detection device is configured to determine the first volume of the liquid disposed in the first compartment by emitting a first signal from the first ultrasound transducer and determining a first height of a first liquid surface by measuring a first time-of-flight of a first signal reflection, and determine the second volume of the liquid disposed in the second compartment by emitting a second signal from the second ultrasound transducer and determining a second height of a second liquid surface by measuring a second time-of-flight of a second signal reflection.

7. The fluid collection system according to claim 1, wherein the detection device is configured to determine a flow rate of liquid entering the collection container by measuring a first change in volume of the first compartment, a second change in volume of the second compartment, a tilt angle of the collection container, and the inversion event.

8. The fluid collection system according to claim 1, wherein the detection device is communicatively coupled with an external computing device.

9. The fluid collection system according to claim 8, wherein the external computing device includes one of an external monitor, a laptop, a computer, a mobile device, a smart phone, a tablet, a "wearable" electronic device, a centralized network server, a decentralized network server, a hospital intranet server, an Electronic Health Record ("EHR") system, a "cloud" based network server, or an internet server.

10. The fluid collection system according to claim 1, wherein the catheter is in fluid communication with the first compartment, the catheter configured to drain the liquid from a cavity of a patient.

11. The fluid collection system according to claim 10, wherein the catheter includes one of an external urinary catheter, an internal urinary catheter, a Foley catheter, a balloon catheter, or a peritoneal catheter.

12. A method of measuring a flow rate of fluid, comprising:
   providing a fluid liquid collection system, comprising:
      a catheter;
      a drainage tube;
      a collection container, including a first compartment in fluid communication with a second compartment;
      a collection bag, wherein the catheter, the drainage tube, the collection container, and the collection bag define a closed liquid collection system; and
      a detection device releasably coupled to an outer surface of the collection container configured to measure a volume of liquid within the collection container without compromising an integrity of the closed liquid collection system;
   directing a liquid to fill the first compartment before filling the second compartment;
   detecting an inversion event of the collection container;
   measuring the volume of liquid disposed in one of the first compartment or the second compartment; and
   providing a message to an external computing device including information about the volume of liquid disposed within the collection container.

13. The method according to claim 12, wherein the external computing device includes one of an external monitor, a laptop, a computer, a mobile device, a smart phone, a tablet, a "wearable" electronic device, a centralized network server, a decentralized network server, a hospital intranet server, an Electronic Health Record ("EHR") system, a "cloud" based network server, or an internet server.

14. The method according to claim 12, wherein the detection device includes one or more sensors configured to detect the inversion event, the one or more sensors includes one of a gyroscope configured to measure a tilt angle of the collection container relative to a vertical axis, or an accelerometer configured to measure a movement of the collection container in three-dimensional space.

15. The method according to claim 12, wherein detecting the inversion event includes measuring one of a surface height of the liquid, a tilt angle, or a movement of the collection container to determine one of:
   i) rotating the collection container through a frontal plane to transfer the liquid between the first compartment and the second compartment; or
   ii) rotating the collection container through a medial plane to transfer the liquid between the second compartment and the collection bag.

16. The method according to claim 12, wherein the collection container further includes a transfer outlet configured to provide fluid communication between the collection container and the collection bag.

17. The method according to claim 12, wherein a first volume of the first compartment is less than a second volume of the second compartment.

18. The method according to claim 12, wherein measuring the volume of liquid disposed in one of the first compartment or the second compartment includes emitting a signal from a transducer and determining a height of a liquid surface by measuring a time-of-flight of a signal reflection.

19. The method according to claim 12, wherein the detection device is configured to determine a flow rate of the liquid entering the collection container by measuring a change in liquid volume disposed within the collection container a tilt angle of the collection container, and the inversion event.

* * * * *